United States Patent [19]

Eichen et al.

[11] Patent Number: 4,594,294
[45] Date of Patent: Jun. 10, 1986

[54] MULTILAYER COATING INCLUDING DISORDERED, WEAR RESISTANT BORON CARBON EXTERNAL COATING

[75] Inventors: Erwin Eichen, West Bloomfield; James Flasck, Rochester, both of Mich.

[73] Assignee: Energy Conversion Devices, Inc., Troy, Mich.

[21] Appl. No.: 658,831

[22] Filed: Oct. 9, 1984

Related U.S. Application Data

[63] Continuation-in-part of Ser. No. 535,352, Sep. 23, 1983.

[51] Int. Cl.$^4$ ............................................. B22F 5/00
[52] U.S. Cl. .................... 428/552; 428/457; 428/698; 423/291; 204/192 SP
[58] Field of Search .............. 428/548, 551, 552, 457, 428/698; 423/291; 204/192 R, 192 SP, 192 C

[56] References Cited

U.S. PATENT DOCUMENTS

| | | | |
|---|---|---|---|
| 3,671,306 | 6/1972 | Allen | 423/291 |
| 3,867,191 | 2/1975 | Galasso et al. | 428/401 |
| 3,967,029 | 6/1976 | Veltri et al. | 428/698 |
| 4,017,587 | 4/1977 | Ditter et al. | 423/291 |
| 4,177,473 | 12/1979 | Ovshinsky | 427/86 X |
| 4,225,355 | 9/1980 | Galasso et al. | 423/291 |
| 4,287,259 | 1/1981 | Riley et al. | 423/291 |
| 4,343,865 | 8/1982 | Graham | 428/552 |

FOREIGN PATENT DOCUMENTS 3206322  9/1982  Fed. Rep. of Germany ...... 423/291

OTHER PUBLICATIONS

Voigt et al., Chem. Abst. 98 (1983), #22012.
Fitzer et al., Chem. Abst. 99 (1983), #126797.
Roth et al., Chem. Abst. 93, (1980), #59239.

*Primary Examiner*—Peter A. Nelson
*Attorney, Agent, or Firm*—Richard M. Goldman

[57] ABSTRACT

A wear resistant multilayer coating is provided. The wear resistant coating comprises at least one internal layer and a thin, external layer of disordered boron and carbon applied to a substrate. The synergistic interaction of a hard internal layer and a lubricious boron and carbon layer provides a long lived tool coating. In a more specific embodiment, the external layer of the coating is disordered boron carbide. In accordance with one embodiment, the disordered boron and carbon external coating is of a composition $B_xC_{1-x}$ where x is from about 0.60 to about 0.90.

8 Claims, 4 Drawing Figures

MULTILAYER COATING INCLUDING DISORDERED, WEAR RESISTANT BORON CARBON EXTERNAL COATING

CROSS REFERENCE TO RELATED APPLICATION

This is a continuation-in-part of our commonly assigned, copending, U.S. application Ser. No. 535,352 filed Sept. 23, 1983 for Disordered Boron-Carbon Wear Resistant Coating and Method.

ART TO WHICH THE INVENTION RELATES

This invention relates to coatings and more particularly to coatings on surfaces that are subjected to friction or wear, and to coatings for tools utilized for cutting, forming and grinding.

BACKGROUND

In the past, tools have been fabricated to achieve various hardness, lubricity and wear characteristics by controlling certain parameters. For example, tools for working and shaping unhardened steels may be fabricated from steel containing enough carbon to form very hard martensite. In more complicated compositions, varying the carbon content and alloy content makes possible non-deforming steels, shock-resistant steels, hot-work steels, or high-speed steels. In some of these steels, alloying elements such as titanium, vanadium, molybdenum, tungsten and chromium are used. These are elements which have a great affinity for carbon and form hard, wear-resistant metallic carbides. However, in many cases, it is desirable to provide a tool having a coating on the surface thereof to improve the hardness and/or lubricity of the tool. This is especially the case where it is desired to lengthen the tool life, or where it is necessary to shape and work hardened steel. However, many refractory hard tool coatings, for example refractory oxides, carbides, nitrides, and borides have a very low lubricity. Moreover, some refractory oxides, e.g., alumina, have a highly irregular topography. The combination of irregular topography and low lubricity militates against the use of certain refractory compounds as tool coatings.

This is also the case where it is desired to provide a hard layer atop an underlying soft, elastic, or deformable layer, where the hard layer protects the substrate from degradation.

A need exists for a wear resistant coating that retains the hardness of refractory compounds while avoiding the low lubricity and irregular topography of many refractory compounds. A need also exists for a wear resistant coating that retains the desirable properties of such refractory coatings as alumina and has improved adhesion properties and resistance to fracture. Similarly, a need exists for a external wear resistant coating atop an underlying soft, deformable, or elastic layer, as a stainless steel or chromium layer.

SUMMARY OF THE INVENTION

In accordance with a broad aspect of the invention, a disordered boron and carbon external coating is provided atop an underlying wear layer, the disordered boron-carbon coating exhibiting excellent resistance to wear. Tools and other articles which are subject to wear, as a result of contact with other surfaces, can be coated with an underlying wear resistant layer and a surface coating of disordered boron and carbon material to increase the useful life of the coated tool or article. The surface wear resistant coating can be boron carbide or a mixture of disordered boron and carbon.

The wear resistant coating is formed as a thin layer on the coated surface of an article such as a tool or other substrate and preferably comprises a coating of boron carbide. As used herein, "substrate" and "article" are interchangeable and include the underlying hard or elastic coating, coatings, or layer other than the external boron-carbide wear resistant coating of the invention.

Tools coated in accordance with the invention utilizing disordered boron and carbon above an underlying coating generally have excellent hardness and lubricity characteristics which result in increased lifetimes and, depending on the particular application, improved surface finishes on parts or workpieces machined therewith.

The wear resistant, disordered, boron and carbon surface coatings can be amorphous, polycrystalline (and lacking long range compositional order), microcrystalline or a mixture of any combination of those phases.

Preferably, the composition of the surface coating is:

$$B_x C_{1-x'}$$

where "B" represents boron, "C" represents carbon and "x" and "1−x" represent the relative amount of boron and carbon respectively, present in the coating, "x" being from about 0.60 to about 0.90. Disordered coatings of boron and carbon on either side of this range are also included within the scope of the invention. Most preferably, the coatings are disordered boron carbide ($B_4C$). Thus, included in accordance with the present invention are coatings which are non-stoichiometric as well as those that are stoichiometric.

The coating of the present invention is disordered when formed. It is believed that a disordered wear resistant coating performs better than a single phase crystalline coating due to diffusive bonding between the substrate surface, i.e., the underlying coating, and the boron-carbide coating, resulting in better adherence. Disordered materials also lack extended lattice planes through which fractures can propagate and in general can withstand relatively high deformation forces without fracture. Such materials are generally less susceptible to corrosion than a single phase crystalline material. It is believed that the foregoing advantages are more fully realized with an amorphous or substantially amorphous external coating.

A nonstoichiometric wear resistant boron-carbide external coating can be utilized in which the coating composition can be tailor-made to achieve desired characteristics while avoiding the formation of extended lattice planes which could adversely affect the adherence, wear resistance or other properties of the coating.

Any suitable method to form the disordered boron-carbide coating can be used. One method of forming the coating is by sputtering. Since sputtering can take place at a relatively low substrate temperature (generally about 200° or less, for example), the coating can be formed while avoiding significant changes in the properties of the substrate material, thereby providing a surface that has increased resistance to wear and excellent lubricity. Accordingly, the invention is particularly useful for coating materials such as coated tool steel, coated tungsten carbide, and coated cemented carbides, e.g., alumina and/or zirconia coated cemented carbides, and TiC containing alumina and/or zirconia coated cemented carbides, since the processing temperature does not degrade the properties of these materials and coatings. Sputtering at low substrate temperature also allows formation of the coating in a disordered state.

The multi-layer coating can be applied to a tool surface or substrate surface as a continuous thin layer without significantly changing the dimensions of the tool since the thickness of the coating can be relatively thin and can be closely controlled. After a tool, with or without a coating, has been in use, a coating in accordance with the invention can be applied thereto, to achieve a desired tolerance or otherwise replace material that has been worn from the tool. Thus, the invention makes possible the reclamation of tools that would otherwise be discarded.

A boron-carbide coating in accordance with the invention can be applied atop a hard coating or atop an elastic coating, achieving excellent adherence for use on tools and other surfaces that are subjected to wear or friction, for example. No adherence coating or layer is required, as the coating of the invention can provide excellent adherence to intermediate hard or elastic coatings. Preferably, the intermediate hard or elastic coating and the external disordered coating are continuous.

In accordance with the invention, a coated article is provided that includes a coated substrate and a boron and carbon containing, external wear resistant coating over at least a portion of the coated substrate. The external coating is a disordered coating of boron and carbon as previously described.

The disordered boron and carbon coating of the invention can be further characterized as being relatively inert and stable, with good resistance to degradation as a result of exposure to, e.g., humidity and heat.

In accordance with another aspect of the invention, a method is provided for making a wear resistant boron and carbon coating, which method is similar to the described general method and comprises depositing over a coated substrate a layer of disordered boron and carbon. The layer of disordered boron and carbon is as previously described.

In accordance with still another aspect of the invention, a method of machining a workpiece is provided. As used herein, "machining" is used in a broad sense and includes, but is not limited to, cutting, grinding, shaping, polishing, reaming, turning, drilling, broaching, sharpening and the like. The method comprises machining a workpiece with an article, such as a tool, for example, having at least a portion of the article or on a working edge or surface thereof, coated with an inner refractory hard coating and an external wear resistant boron and carbon coating in accordance with the invention.

DETAILED DESCRIPTION

Figure 1:
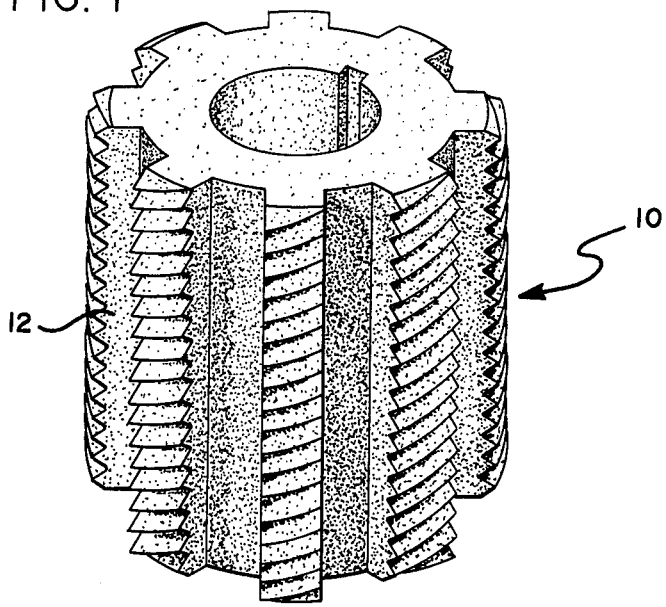
FIGS. 1-4 illustrate in perspective view tools which may have wear resistant coatings in accordance with the invention.

The disordered wear resistant external surface coating of the invention is preferably formed by sputtering, although any suitable technique which forms a disordered coating of boron and carbon having suitable adherence to the underlying coating and physical integrity can be utilized. The preferred type of sputtering is dc magnetron sputtering with a bias voltage. Sputtering allows the coating to be applied at relatively low temperature and is less likely to affect the substrate properties than other techniques which require relatively high temperature.

While sputter depositing techniques are generally known to those skilled in the art, to maximize the benefits of the invention, it is advantageous to form the desired coating with a sputtering technique that is adapted to the particular geometry of the surface to be coated. Usually, a dc or rf bias is applied to the substrate during application of the coating by sputtering. The bias may improve adhesion of the coating formed on the the substrate, reduce stress in the coating and increase the density of the coating. The substrate geometry in part determines the most desirable sputtering technique for a particular application.

Prior to sputter depositing, it is important to provide an atomically clean surface on the portion of the underlying tool coating that is to be coated. This facilitates the formation of a uniform external boron-carbide coating which adheres to the underlying coating. There are several methods known to those skilled in the art for providing an atomically clean surface for sputtering and any such method may be utilized. The following surface preparation method is provided by way of example only and is not to be construed as a limitation upon the present invention.

In accordance with one method for providing an atomically clean surface, the refractory coated or elastic metal coated substrate is cleaned with a chlorinated hydrocarbon degreaser. Thereafter, the refractory coated or elastic metal coated substrate is rinsed in methanol and is then subjected to either plasma or dry chemical etching. When plasma etching is utilized, preferably a fluorinated carrier gas, such as carbon tetrafluoride is utilized. The carrier gas decomposes and provides fluorine which cleans the substrate surface. The final step for providing an atomically clean surface for the coating is sputter etching in an argon plasma.

After an atomically clean surface has been provided on the coated substrate or at least on that portion of the coated substrate which is to be coated with the boron and carbon exterior coating, the wear resistant boron and carbon coating can be applied.

Generally, the wear resistant, external, boron and carbon containing coating is applied by sputtering. The preferred sputtering conditions depend on surface geometry and the type of microstructure desired. Generally, however, it is desirable for the surface of the wear resistant boron and carbon coating to be smooth, especially for many wear-related applications. The internal microstructure of the disordered wear resistant coating may be columnar or non-columnar. For some applications, a columnar surface of the wear resistant coating can be desirable.

When it is desired to produce a columnar microstructure, any type of sputtering technique known in the art which produces a columnar microstructure can be utilized. One technique for producing a columnar microstructure applies sufficient bias voltage to the substrate to cause formation of the columnar microstructure. For some coating materials and/or substrate geometries, a columnar microstructure may not be formed, even with a high bias voltage. As is known to those skilled in the art, bias sputtering is the process of maintaining a negative bias voltage on the substrate during deposition.

By applying a bias voltage to the substrate, the density, purity, adhesion and internal stress of the coating can be controlled. Generally, application of a bias voltage tends to increase the density, purity and adhesion and also tends to decrease the internal stress of the coating.

The bias voltage applied to a substrate during sputtering may be varied in a desired sequence. The preferred bias sequencing depends on the substrate geometry and the desired microstructure. For complex shapes, or for surfaces having a relatively high (about 2.0 or greater) aspect ratio (which is the ratio of the macroscopic depth to the width of a surface, e.g. the aspect ratio of a planar surface is 0 and the aspect ratio of a surface having a depression whose depth equals its width is 1), it is desirable to initially sputter the boron and carbon coating material onto the coated substrate at a relatively low bias voltage (for example, about −100 to −200 volts) to insure complete coverage. Thereafter, the bias voltage is increased to a relatively high bias voltage (for example, about −1000 to −2500 volts). The biasing voltage can be gradually increased (ramp increased) or step increased. Utilizing such bias voltage tends to promote a more dense, purer coating having greater adhesion to the underlying layer, less internal stress and also tends to promote columnar growth. It is believed that a columnar microstructure generally results in better adherence, possibly as a result of mechanical anchoring to the underlying layers. For the exterior coating surface applied to a surface with a high aspect ratio, the bias voltage can be applied as for the underlying portion of the coating, except that if a smooth surface is desired, towards the end of the deposition the bias voltage is lowered (for example, generally to about −100 to −200 volts) or eliminated, which tends to allow formation of a smooth surface.

For surface having an aspect ratio of about 0.5 to about 2.0, the layers are preferably sputtered at essentially a constant bias voltage, generally between −500 and −1000 volts. A higher voltage can be used. For the exterior layer, the bias voltage should be adjusted such that a relatively smooth surface is provided, if this is desired.

For surfaces having relatively low aspect ratios (between 0 and about 0.5), preferably the bias voltage initially is higher (about −1000 to −2500 volts) and can be decreased to low voltage (about −100 to −200 volts) in either step or ramp fashion, or eliminated. Again, the decrease or elimination of bias voltage usually applies towards the end of the deposition of the coating. Decreasing or relatively low bias voltage also tends to promote a relatively smooth surface which generally results in a more lubricious surface, which can be desirable in many cases.

Since sputtering can take place at relatively low substrate temperatures (generally about 200° C. or less, for example), the coatings can be formed while avoiding significant changes in the properties of the substrate material while providing a surface that has increased resistance to wear and excellent lubricity. Accordingly, the invention is particularly useful for coating materials such as tool steel, tungsten carbide and cemented carbides, graphite, plastics and other substrates where either the substrate or intermediate coating layers can be adversely affected by elevated temperature, for example, since the processing temperature does not degrade the properties of these materials. Sputtering at low substrate temperatures also allows formation of the coatings in a disordered state. The invention is also suitable for coating precisely dimensioned substrates, regardless of substrate composition.

To produce sputtered disordered coatings, generally the sputtering will take place at substrate surface temperatures of less than about 200° C. and usually at about 100° C. or even less, to facilitate formation of disordered coatings. Thus, the coatings in accordance with the present invention can be formed at relatively low temperatures. The target generally is also cooled to prevent evaporation, melting or other unwanted degradation of the target. As a result, the coating is applied to a tool surface, for example, without significantly altering physical properties of the tool, such as the dimensions, hardness and transverse rupture strength. Generally, substrate temperatures, target compositions, deposition rates and gas pressures which tend to prevent the formation of disordered coatings should be avoided.

It is usually desirable to form a wear resistant coating that is between about one (1) and about eight (8) micrometers in thickness, with a thickness of about 2.5 micrometers usually being a good thickness for use on tools. Coatings having a thickness in excess of about eight (8) micrometers may not be particularly desirable in applications where high tolerance must be maintained since the geometry and/or size of the tool and parts resulting therefrom may be altered. The sputtering technique can be chosen in accordance with the guidelines hereinafter set forth relating to relatively simple and complex substrate surface geometries.

The underlying layer or coating may be harder and less lubricious than the boron and carbon coating, as a stochiometric or non-stochiometric refractory compound. Exemplary compounds include both stochiometric and non-stochiometric compounds referred to as titanium carbide, titanium boride, titanium nitride, tungsten boride, tungsten carbide, molybdenum boride, diamond-like carbon, alumina, zirconia, silicon nitride, silicon carbide, boron nitride, tantalum carbide, and combinations thereof. For example, there may be discrete layers of refractory compounds in the underlying coating, e.g., discrete layers of alumina, carbides, and nitrides. Exemplary is an insert having successive layers of titanium carbide, alumina, and titanium nitride, or of titanium nitride, titanium carbide, alumina, and titanium nitride.

The underlying coating may contain several individual layers, e.g., up to eight (8) or ten (10) or more. Individual layers may be from 500 Å to 10 or more microns thick, with a total thickness of from 2000 Å to 50 microns or more.

The underlying may contain metals or compounds that are more elastic and/or deformable than the contemplated external coating, e.g., the underlying coating may be stainless steel or chromium, or even silver or copper, and be more elastic, more deformable, or more ductile then the boron-carbon external coating.

It is to be understood that the coatings and methods described herein can be utilized on tools that have been subjected to use, either with or without the multi-layer coatings described herein. For example, after a tool having a multi-layer coating in accordance with the invention has been in use, and is either worn or outside of a desired tolerance range, the coating in accordance with the invention can be applied to the tool, resulting in an increased tool life. Also, a coating can be applied to tools which did not previously have a coating of the invention thereon. Thus, tools which would otherwise be discarded can be reclaimed.

Referring now to FIGS. 1-4, several types of tools are illustrated which can be coated in accordance with the present invention.

In FIG. 1, there is illustrated a gear hob 10 which can be coated in accordance with the present invention. Gear hob 10 has a plurality of radially extending teeth 12 and is one example of a complex surface.

Figure 2:
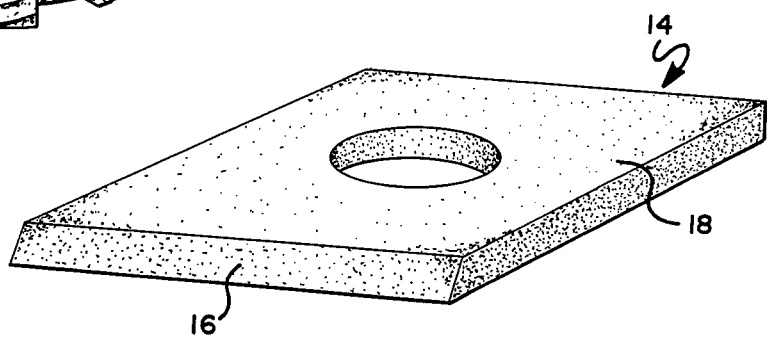

FIG. 2 is a perspective view of an insert tool 14 having a flank face 16 and a rake face 18. The substrate of insert tool has been coated over its entire surface with a wear resistant coating of topography modifying and adhesion layers, a refractory hard layer, and the herein contemplated layer of boron and carbon, i.e., titanium-nitrogen, titanium-carbon, aluminum and titanium-nitrogen layers, and an external boron-carbon layer.

Figure 3:
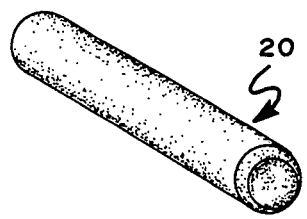

FIG. 3 is a perspective view of a bearing pin 20. Bearing pin 20 is an example of a relatively simple surface.

Figure 4:
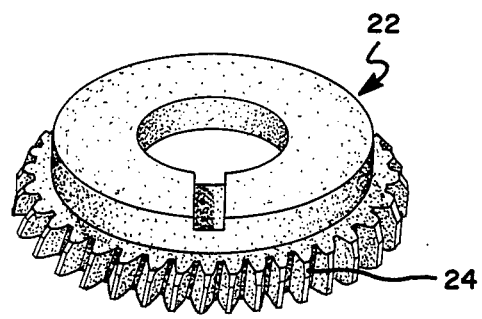

FIG. 4 illustrates a gear shaver tool 22 which is composed of a plurality of radially extending teeth 24. Gear shaver tool 22 illustrates another relatively complexly surfaced tool for which the method and coatings in accordance with the present invention are suitable.

Generally, the hardness of the boron carbide coatings in accordance with the present invention is about KHN (50 grams)=4,700 kg/mm$^2$ as measured on a 50 micron thick (boron carbide) coating that was substantially amorphous with some microcrystalline material. Since the disordered coatings are generally relatively thin, direct measurement of a typically used thickness is impractical. It is expected that thinner coatings would have about the same hardness. However, in addition to being relatively hard, the coatings of the present invention generally also exhibit excellent lubricity. As a result, tools in accordance with the present invention have increased life and the use of such tools can result in an improved surface finish on parts machined therewith.

The present invention and its advantages can be more completely understood from the following example:

EXAMPLE 1

A series of cemented carbide inserts were prepared having a boron carbide external coating atop sequential titanium nitride, titanium carbide, alumina, and titanium nitride layers.

The cemented carbide inserts were SANDVIK AB type RNMA 43GC415 tapered tool inserts, 3/16 inch (4.7 mm) high by ½ inch (12.7 mm) diameter. The inserts had an inner layer, less than 1 micron thick, of titanium nitride, a 2 micron layer of titanium carbide atop the titanium nitride layer, a 5 micron layer of alumina atop the titanium carbide layer, and an external, one micron, layer of titanium nitride. All of the layers had been applied by chemical vapor deposition.

The inserts were then coated by D.C. magnetron sputtering. The sputtering target was B$_4$C, formed by hot pressing 99 percent pure, crystalline B$_4$C powder. Disordered boron carbide coatings approximately 2.5 microns thick were deposited atop the titanium nitride-titanium carbide-alumina-titanium nitride coated, cemented tool inserts.

The inserts were tested for their ability to remove a 0.100 inch 964L weldment from a four inch (10 cm) high, 25 inch (63.5 cm) diameter die. The weldment had a Rockwell C hardness of 54 to 58.

Metal removal was carried out to remove a 0.100 inch (2.54 mm) cut depth of weldment along the perimeter of the die. The following results were obtained:

| Coating | As received | As received + B$_4$C | As received + B$_4$C |
| --- | --- | --- | --- |
| Revolutions per minute | 9 | 21 | 25 |
| Workpiece speed (ft/min) | 58.1 | 137.4 | 163.6 |
| Metal Removal (in$^3$/min) | 0.088 | 2.639 | 3.927 |
| Time to attain 0.100 inch removal (min) | 356 | 11 | 8 |

Multi-layer coatings of disordered boron and carbon of desired proportions can be made using similar techniques and appropriately choosing the target composition. Also, multiple targets or different elements or compositions could be utilized. While the foregoing examples have shown production of the disordered coating materials by sputtering techniques, the invention is not so limited. Any method which produces a coating having the desired degree of disorder (amorphous, polycrystalline, microcrystalline or any combination thereof) can be utilized. By the term "amorphous" is meant a material which has long range disorder, although it may have short or intermediate order or even contain at times some crystalline inclusions.

It is to be understood that the coatings of the present invention are not limited to applications involving tools. The invention is useful on surfaces that may be subjected to friction or wear, including, for example, and not as a limitation on the invention, bearings, engine parts, fittings, and other devices where friction or wear is encountered.

While this invention has been described in relation to its preferred embodiments, it is to be understood that various modifications thereof will be apparent to those of ordinary skill in the art upon reading this specification and it is intended to cover all such modifications as fall within the scope of the appended claims.

We claim:
1. A coated article comprising:
   (a) a substrate;
   (b) a multilayer coating on said substrate, said multilayer coating comprising:
      (i) a first titanium nitride layer on the substrate;
      (ii) a titanium carbide layer atop the first titanium nitride;
      (iii) an alumina layer atop the titanium carbide layer;
      (iv) a second titanium nitride layer atop the titanium carbode layer; and
      (v) an external layer of disordered boron and carbon.

2. The coated article of claim 1 wherein the external layer has composition on an atomic basis of B$_x$C$_{1-x}$ where x is from about 0.60 to about 0.90.

3. The coated article of claim 2 wherein the disordered boron and carbon comprises amorphous material.

4. The coated article of claim 2 wherein the disordered boron and carbon comprises polycrystalline material.

5. The coated article of claim 2 wherein the disordered boron and carbon comprises microcrystalline material.

6. The coated article of claim 2 wherein the disordered boron and carbon comprises at least one phase selected from the group consisting of amorphous, microcrystalline, and polycrystalline phases.

7. The coated article of claim 2 wherein the disordered boron and carbon is substantially amorphous.

8. The coated article of claim 2 wherein the disordered boron and carbon comprises disordered boron carbide.

* * * * *